United States Patent
Mori et al.

(10) Patent No.: US 11,690,494 B2
(45) Date of Patent: Jul. 4, 2023

(54) ENDOSCOPE OBSERVATION ASSISTANCE APPARATUS AND ENDOSCOPE OBSERVATION ASSISTANCE METHOD

(71) Applicants: Showa University, Tokyo (JP); National University Corporation Tokai National Higher Education and Research System, Nagoya (JP)

(72) Inventors: Yuichi Mori, Yokohama (JP); Shin-ei Kudo, Yokohama (JP); Masashi Misawa, Yokohama (JP); Kensaku Mori, Nagoya (JP)

(73) Assignees: SHOWA UNIVERSITY, Tokyo (JP); NATIONAL UNIVERSITY CORPORATION TOKAI NATIONAL HIGHER EDUCATION AND RESEARCH SYSTEM, Nagoya (JP)

( * ) Notice: Subject to any disclaimer, the term of this patent is extended or adjusted under 35 U.S.C. 154(b) by 359 days.

(21) Appl. No.: 17/046,233

(22) PCT Filed: Apr. 12, 2019

(86) PCT No.: PCT/JP2019/015925
§ 371 (c)(1),
(2) Date: Oct. 8, 2020

(87) PCT Pub. No.: WO2019/198808
PCT Pub. Date: Oct. 17, 2019

(65) Prior Publication Data
US 2021/0022586 A1    Jan. 28, 2021

(30) Foreign Application Priority Data
Apr. 13, 2018    (JP) ................. 2018-077624

(51) Int. Cl.
*A61B 1/00* (2006.01)
*A61B 1/045* (2006.01)

(52) U.S. Cl.
CPC .... *A61B 1/000094* (2022.02); *A61B 1/00006* (2013.01); *A61B 1/00045* (2013.01); *A61B 1/045* (2013.01); *A61B 1/00039* (2013.01)

(58) Field of Classification Search
CPC .......... A61B 1/000094; A61B 1/00006; A61B 1/00045; A61B 1/045; A61B 1/00039;
(Continued)

(56) References Cited

U.S. PATENT DOCUMENTS

| 4,196,412 A | 4/1980 | Anderson et al. |
| 5,740,801 A * | 4/1998 | Branson ................. G16H 20/40 600/407 |

(Continued)

FOREIGN PATENT DOCUMENTS

| JP | 2010035756 A | 2/2010 |
| JP | 2015112429 A | 6/2015 |

(Continued)

OTHER PUBLICATIONS

Japanese Office Action from corresponding Japanese Application No. 2018-077624, dated Jul. 20, 2021, 2 pages.
(Continued)

*Primary Examiner* — Timothy J Neal
*Assistant Examiner* — James Edward Boice
(74) *Attorney, Agent, or Firm* — Tucker Ellis LLP

(57) ABSTRACT

An endoscope observation assistance apparatus includes an image information acquiring part to acquire and display a captured image of a luminal organ captured by the endoscope device on a display, a lesion information acquisition part to detect a predetermined lesion based on the captured image and to acquire lesion information regarding the
(Continued)

lesion, a lesion disappearance determination part to track the lesion based on the captured image and the lesion information and to determine whether or not the lesion has disappeared from the captured image, and a notification part to notify a determination result when the lesion disappearance determination part determines that the lesion has disappeared from the captured image. Alternatively, the notification part may notify a lesion detection when a short time period passes after the lesion detection by the lesion information acquisition part.

4 Claims, 5 Drawing Sheets

(58) Field of Classification Search
CPC ........ A61B 1/0005; G06T 2207/10068; G06T 2007/30028; G06T 2207/30032
USPC .................................................. 600/103, 117
See application file for complete search history.

(56) References Cited

U.S. PATENT DOCUMENTS

| | | |
|---|---|---|
| 2006/0115146 A1 | 6/2006 | Ogura |
| 2009/0063118 A1 | 3/2009 | Dachille et al. |
| 2011/0032347 A1* | 2/2011 | Lacey .................... G06T 7/0012 |
| | | 348/E7.085 |
| 2011/0254937 A1 | 10/2011 | Yoshino |
| 2012/0220840 A1 | 8/2012 | Morita |
| 2012/0274754 A1 | 11/2012 | Tsuruoka |
| 2014/0184790 A1 | 7/2014 | Ishihara |
| 2015/0078615 A1* | 3/2015 | Staples, II ................ G06T 7/50 |
| | | 382/103 |
| 2018/0098690 A1 | 4/2018 | Iwaki |
| 2018/0114319 A1* | 4/2018 | Kono ..................... A61B 1/018 |
| 2018/0177446 A1 | 6/2018 | Okabe |
| 2018/0253839 A1* | 9/2018 | Zur ....................... G06T 7/0012 |
| 2018/0263568 A1* | 9/2018 | Yi ..................... A61B 1/000094 |
| 2019/0069757 A1 | 3/2019 | Iwaki |
| 2020/0037856 A1* | 2/2020 | Watanabe .............. A61B 1/045 |
| 2020/0237184 A1* | 7/2020 | Shigeta ................ A61B 1/0005 |
| 2021/0022586 A1 | 1/2021 | Mori |

FOREIGN PATENT DOCUMENTS

| | | |
|---|---|---|
| JP | 2016066188 A | 4/2016 |
| JP | 2017068360 A | 4/2017 |
| JP | 2019180966 A | 10/2019 |
| WO | 2016199273 A1 | 12/2016 |
| WO | 2017203560 A1 | 11/2017 |

OTHER PUBLICATIONS

Japanese Office Action from corresponding Japanese Application No. 2021-187092, dated Oct. 11, 2022, 6 pages with translation.
Japanese Office Action from corresponding Japanese Application No. 2021-187093, dated Oct. 11, 2022, 8 pages.
The Extended European Search Report from corresponding European Application No. 19785266.8, dated Feb. 22, 2022, 10 pages.
International Search Report from corresponding International Patent Application No. PCT/JP2019/015925 dated Jul. 2, 2019, 8 pages including translation.
Tran, Du et al., "Learning Spatiotemporal Features with 3D Convolutional Networks", Computer Vision (ICCV), 2015, 9 pages.
Japanese Office Action from corresponding Japanese Application No. 2018-077624, dated Mar. 16, 2021, 3 pages.

* cited by examiner

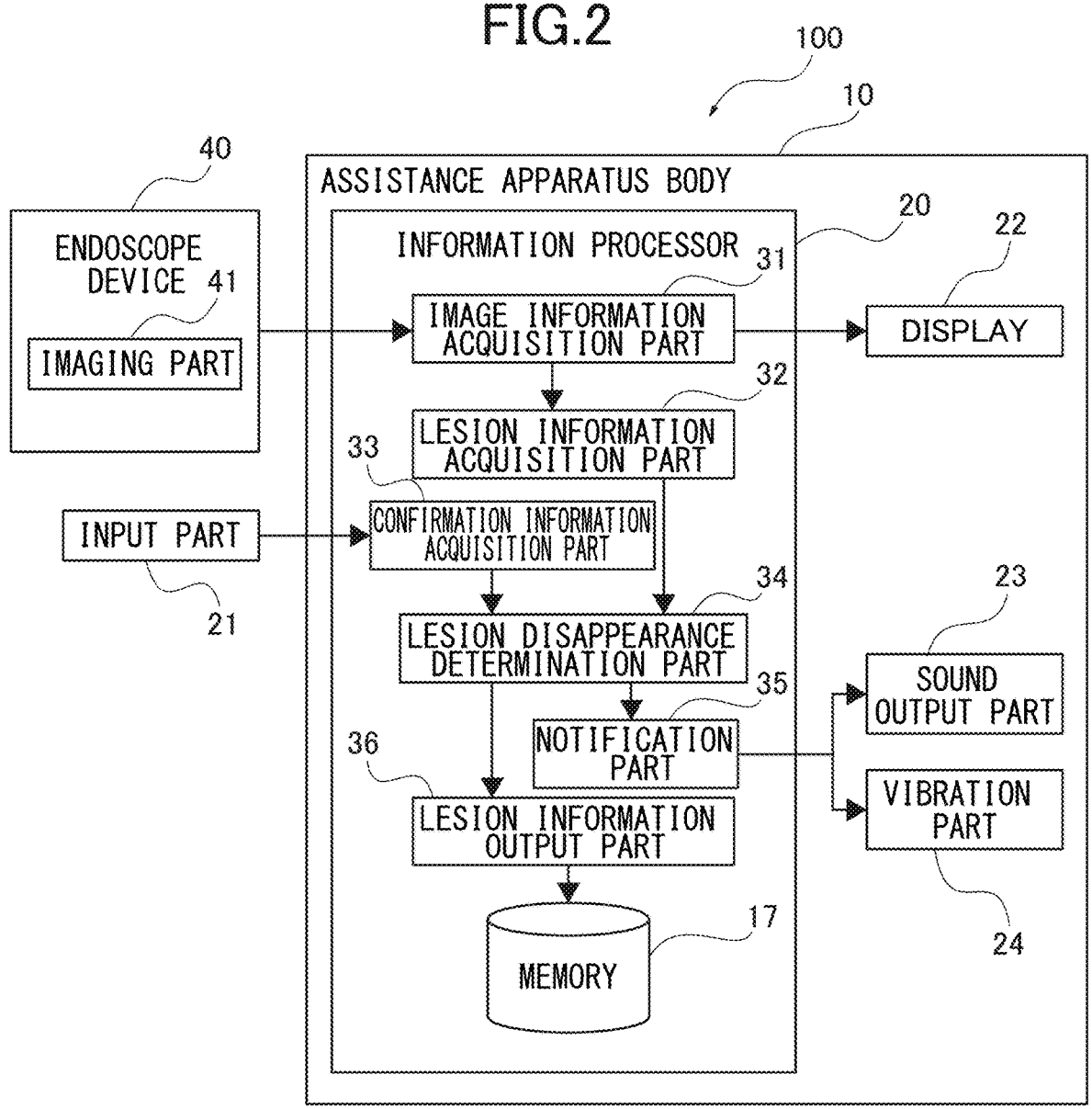

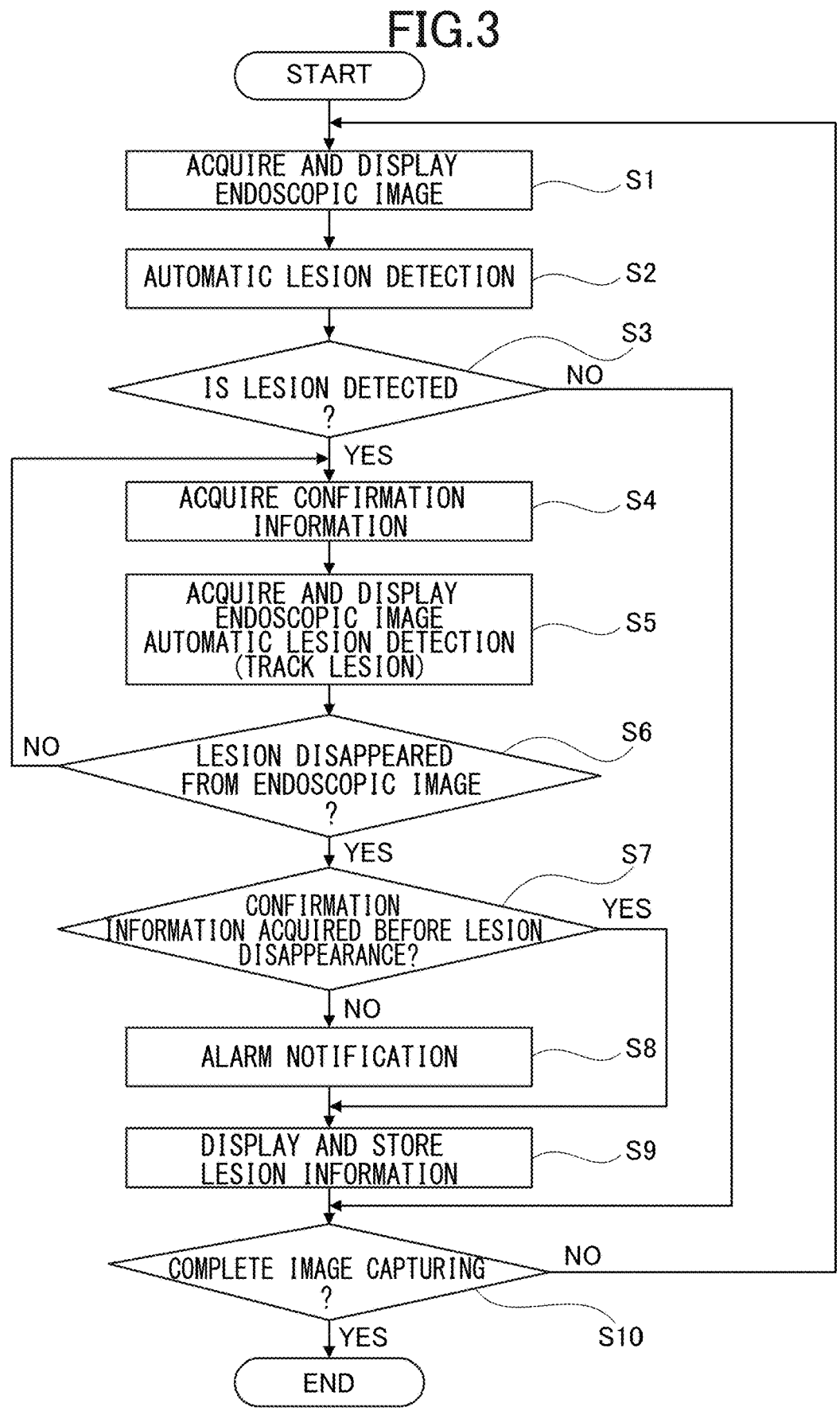

LESION

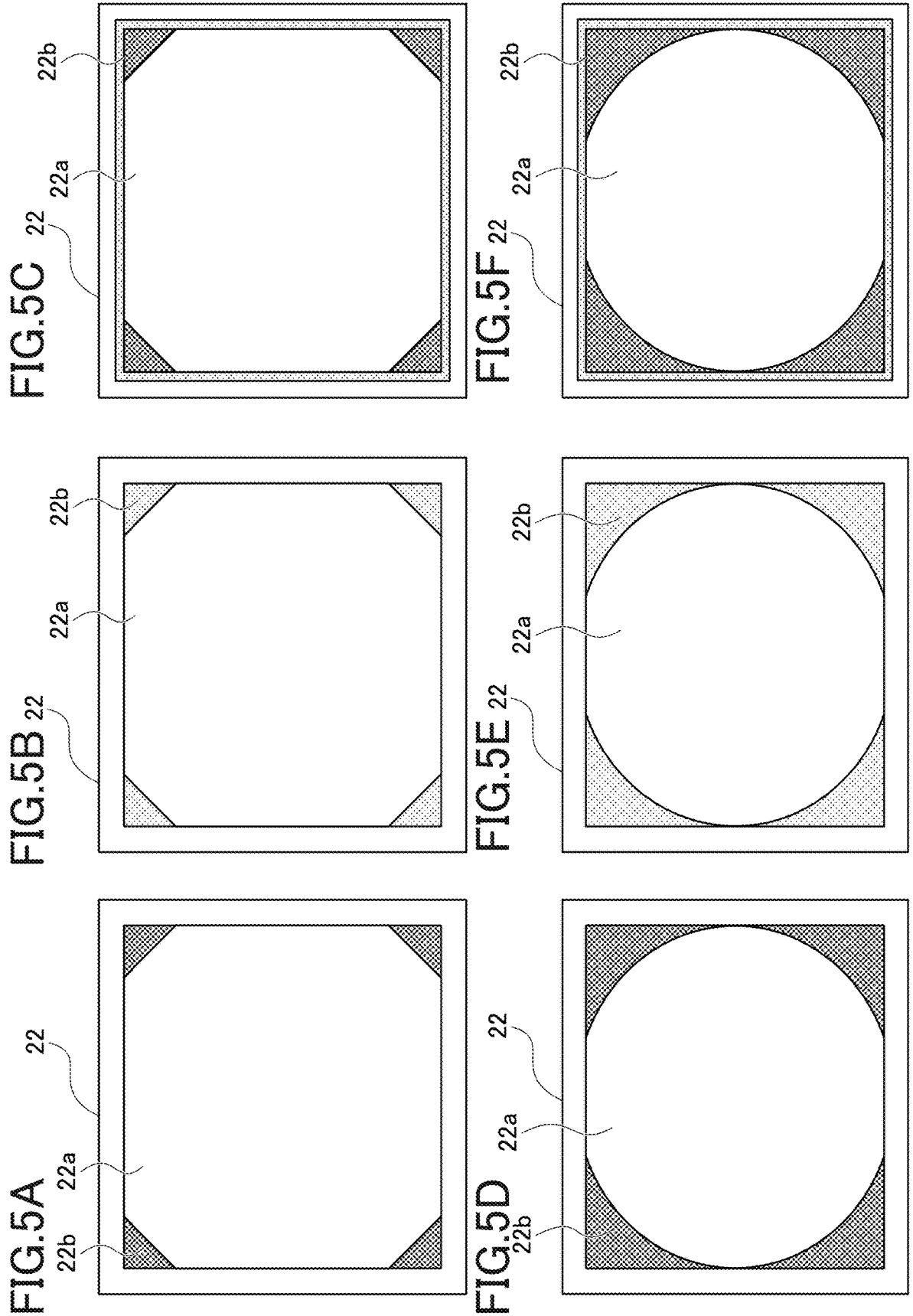

ENDOSCOPE OBSERVATION ASSISTANCE APPARATUS AND ENDOSCOPE OBSERVATION ASSISTANCE METHOD

RELATED APPLICATION DATA

The present application is based on and claims priority to Japanese Patent Application No. 2018-077624, filed on Apr. 13, 2018, the disclosure of which is hereby incorporated by reference in its entirety.

TECHNICAL FIELD

This invention relates to an endoscope observation assistance apparatus, an endoscope observation assistance method, and a program thereof.

BACKGROUND ART

An image processing device, which performs image recognition processing on an endoscopic image of luminal organs, such as digestive organs, and automatically detects tumors, polyps, and other lesions by means of learning functions such as artificial intelligence (AI), has been provided (see JP2006-153742 A, for example).

Additionally, a technology for assisting pathological diagnosis, which gives an alert (e.g., presentation of image of lesion location, presentation of scattered probability, voice alert) to the operator, such as a doctor, in real time in response to automatic detection of a lesion based on an image so as to prevent doctors from overlooking the lesion, has been disclosed (see JP2011-104016 A, for example).

With the development of the artificial intelligence (AI), the accuracy and speed of automatic lesion detection with a computer have improved, thereby contributing to the observation and diagnosis of lesions made by doctors. Tran, Du, et al. "*Learning spatiotemporal features with 3d convolutional networks.*" *Computer Vision (ICCV), 2015 IEEE International Conference on. IEEE,* 2015 teaches that a more accurate image analysis is possible by analyzing a plurality of frames with AI. Therefore, it is desirable to develop a technology that assists doctors to observe and diagnose lesions more accurately by utilizing the detection results obtained by AI without being unnecessarily affected by such detection results.

SUMMARY

The present disclosure has been made in view of the above circumstances, and therefore, an object of the present disclosure is to improve the performance of endoscopic observation assistance so as to realize the observation of lesions made by a doctor more easily and accurately.

In order to achieve the object, an endoscope observation assistance apparatus of the present disclosure is configured to assist observation of a luminal organ with an endoscope and includes an image information acquisition part configured to acquire a captured image of the luminal organ captured by the endoscope and to display the captured image on a display, a lesion information acquisition part configured to detect a predetermined lesion based on the captured image and to acquire lesion information regarding the lesion, a determination part configured to track the lesion based on the captured image and the lesion information and to determine whether or not the lesion has disappeared from the captured image, and a notification part configured to issue a notification of a determination result when the determination part determines that the lesion has disappeared from the captured image.

With the present disclosure, it is possible to improve the performance of endoscopic observation so as to realize the observation of lesions made by a doctor more easily and accurately.

BRIEF DESCRIPTION OF DRAWINGS

FIG. 2 is a functional block diagram of the endoscope observation assistance apparatus of FIG. 1. FIG. 3 is a flowchart for explaining an example of an endoscope observation assistance process executed by the endoscope observation assistance apparatus of FIG. 1. In FIG. 4A, a lesion is found in the endoscopic image. In FIG. 4B, a lesion has disappeared from the endoscopic image. FIGS. 5A-5F are views illustrating examples on the display to alert. FIG. 5A is an example before detecting a lesion (no lesion), FIG. 5B is an example in which a lesion has disappeared from the display after detecting the lesion, FIG. 5C is a variant of the example in which a lesion has disappeared from the display after detecting the lesion, FIG. 5D is a variant of the example before detecting a lesion (no lesion), FIG. 5E is another example in which a lesion has disappeared from the display after detecting the lesion, and FIG. 5F is a variant of said another example in which a lesion has disappeared from the display after detecting the lesion.

DESCRIPTION OF EMBODIMENTS

First Embodiment

Hereinafter, an endoscope observation assistance apparatus according to an embodiment of the present disclosure will be described with reference to the drawings.

Figure 1:
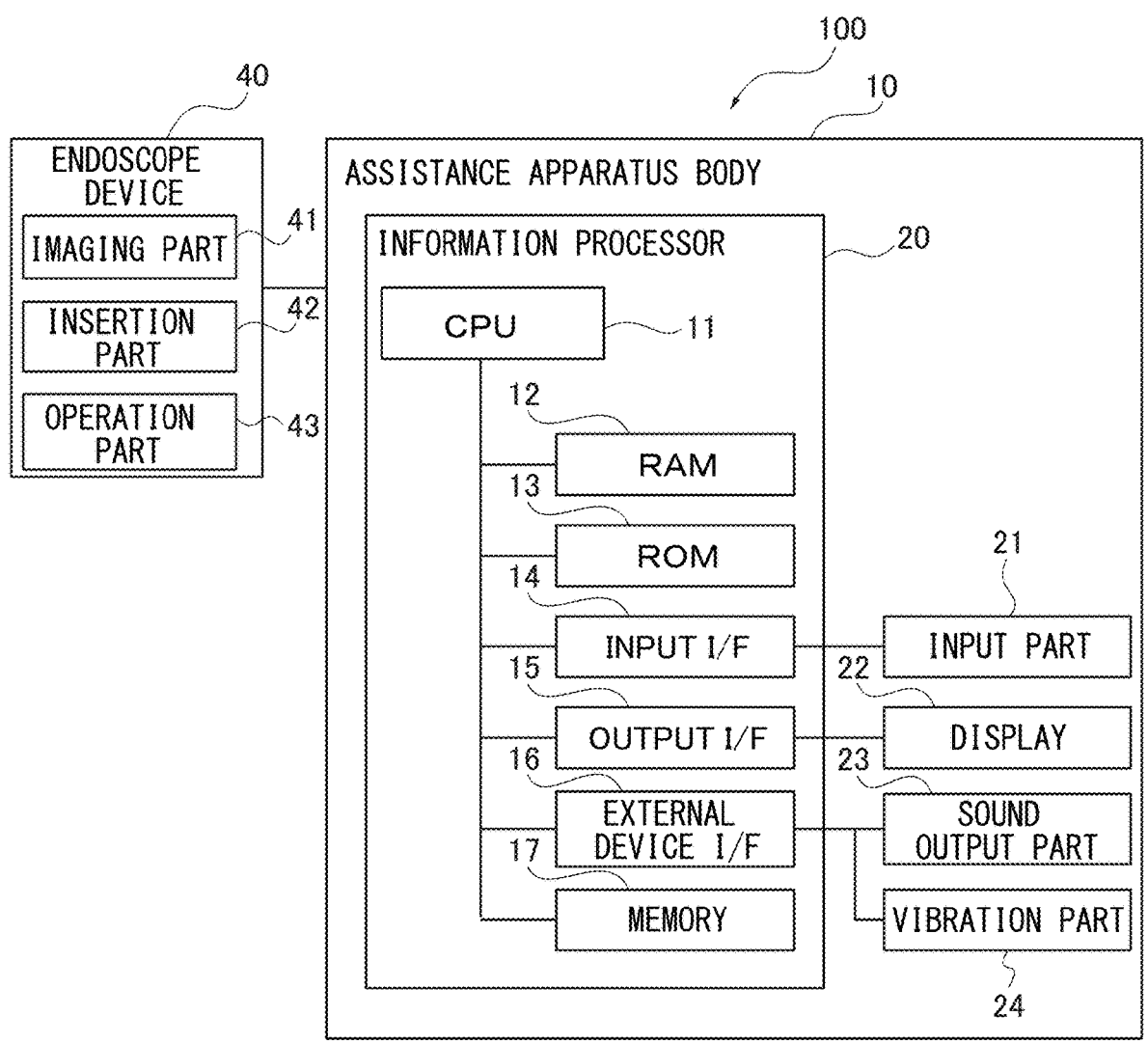
FIG. 1 is a schematic view showing a hardware configuration of an endoscope observation assistance apparatus according to an embodiment of the present disclosure.

FIG. 1 is a schematic view showing a hardware configuration of the endoscope observation assistance apparatus 100 according to this embodiment.

As shown in FIG. 1, the endoscope observation assistance apparatus 100 is mainly configured with an assistance apparatus body 10 and an endoscope device 40.

As illustrated in FIG. 1, the assistance apparatus body 10 includes, for example, an information processor 20, an input part 21, a display 22, a sound output part 23, and a vibration part 24. The information processor 20 includes, for example, a CPU 11, a ROM 12, a RAM 13, an input I/F (interface) 14, an output I/F 15, an external device I/F 16, and a memory 17. The assistance apparatus body 10 may further include a printer to print an endoscopic image and assistance results, as well as a communication device to communicate with the outside.

The information processor 20 may be configured with, for example, a personal computer (PC) or a microcomputer. The CPU 11 is a central processing unit that is configured to control the entire operations of the endoscope observation assistance apparatus 100. The ROM 12 is a read-only memory that stores programs to be executed by the CPU 11, such as a control program and an endoscope observation assistance program. The RAM 13 is a random-access memory that reads and writes data as needed and is used as a work area for the CPU 11. That is, the CPU 11 uses the RAM 13 as the work area and executes the endoscope observation assistance program stored in the ROM 12 to operate the endoscope observation assistance apparatus 100.

The memory 17 is configured with a recording medium, such as a hard disc and a flash memory, and stores various information necessary for the endoscope observation assistance process, calculation results, and the like. The input I/F 14 is an interface for connecting the input part 21 and the CPU 11. The output I/F 15 is an interface for connecting the display 22 and the CPU 11. The external device I/F 16 is an interface for connecting an external device and the CPU 11. In this embodiment, the endoscope device 40, the sound output part 23, and the vibration part 24 are connected to the CPU 11 through the corresponding external I/Fs 16.

The input part 21 is a device to input letters, numbers, and various commands by the operator of the endoscope device 40, such as a doctor. For example, a keyboard, a mouse, a numeric keypad, and/or a touch panel may be used as the input part 21. Doctors may input commands through the input part 21 to capture and record still images of lesions and/or commands to confirm automatically detected lesions.

The display 22 is a device to display, for example, a menu screen, an operation screen, and an endoscopic image (captured image), such as a video image and a still image, captured by the endoscope device 40. For example, a liquid crystal display (monitor) may be used as the display 22.

The sound output part 23 and the vibration part 24 are used for giving a notification (alarm notification) to a doctor. The sound output part 23 is a device to output, for example, a notification sound (alarm sound) and a notification message (alarm message) for drawing doctor's attention. For example, a speaker to output a sound or a voice, and a buzzer may be used as the sound output part 23. The vibration part 24 is a vibrating body that generates vibration applied to the doctor's body. For example, a vibrator for generating vibration with a motor may be used as the vibration part 24. The vibration part 24 is preferably configured to be attached to the doctor's body so as to apply the vibration directly to the doctor's body. Alternatively, the vibration part 24 may be provided to the endoscope device 40 to apply the vibration to the doctor's hand which grips the endoscope device 40 unless it disturbs the operation of the endoscope device 40.

In this embodiment, the endoscope observation assistance apparatus 100 includes both the sound output part 23 and the vibration part 24. However, as long as it is possible to draw the doctor's attention with the alarm notification, the apparatus 100 may include only one of them. For example, by sending the alarm notification with vibration only, it is possible to prevent the patient from realizing that the lesion has been detected. Additionally, an alarm notification may be displayed on the display 22 such that it would be possible to draw the doctor's attention visually in addition to sound and/or vibration.

The endoscope device 40 is a device used for observing and treating luminal organs and is configured with, for example, an electronic scope or a fiber scope. The endoscope device 40 of this embodiment includes, for example, an imaging part 41, an insertion part 42, and an operation part 43. The endoscope device 40 further includes components that may be included in a known endoscope device, such as a water or air supply unit, a suction unit, and a treatment tool, such as forceps used for tissue collection or other treatment.

The imaging part 41 is a device to capture an endoscopic image, such as an in-vivo video image and an in-vivo still image, and is configured with, for example, a CCD camera, a condenser lens, an eyepiece lens, a light source, a light guiding optical system, and an image sensor. The insertion part 42 is configured with a tubular member having flexibility to bend freely and is provided with the CCD camera and the condenser lens of the imaging part 41 at the distal end. Further, the insertion part 42 is provided with, for example, a nozzle from which air and/or water are discharged, as well as a hole through which a treatment tool goes in and out. The operation part 43 is provided with various operation buttons and operation switches to perform, for example, bending operation of the insertion part 42, air supply, water supply, and suction.

The endoscope device 40 is electrically connected to the assistance apparatus body 10 via, for example, a connection cable. The image signals of the endoscopic image captured by the imaging part 41 are output to the assistance apparatus body 10 in real time.

The endoscope device 40 is not particularly limited, and a known device may be used. For example, a laryngoscope for observing nasal cavity, pharynx, larynx, and esophagus; a bronchoscope for observing trachea and bronchus; an upper gastrointestinal endoscope for observing esophagus, stomach, and duodenum; a small intestine endoscope for observing small intestine; a colonoscope for observing large intestine; a biliary endoscope for observing bile duct; a pancreatic duct endoscope for observing pancreatic duct; a thoracoscope for observing inside of chest cavity; a laparoscope for observing inside of abdominal cavity; a cystoscope for observing urethra and bladder; an arthroscope for observing a joint; and a vascular endoscope for observing coronary arteries may be used as the endoscope device 40, but is not limited to these examples.

Additionally, the endoscope device 40 may preferably be a high definition endoscope but is not limited thereto.

Next, the functions of the information processor 20 for controlling the operations of the assistance apparatus body 10 will be described with reference to the functional block diagram of FIG. 2. As illustrated in FIG. 2, the information processor 20 functions as an image information acquisition part 31, a lesion information acquisition part 32, a confirmation information acquisition part 33, a lesion disappearance determination part 34, a notification part 35, and a lesion information output part 36.

Figure 4A:
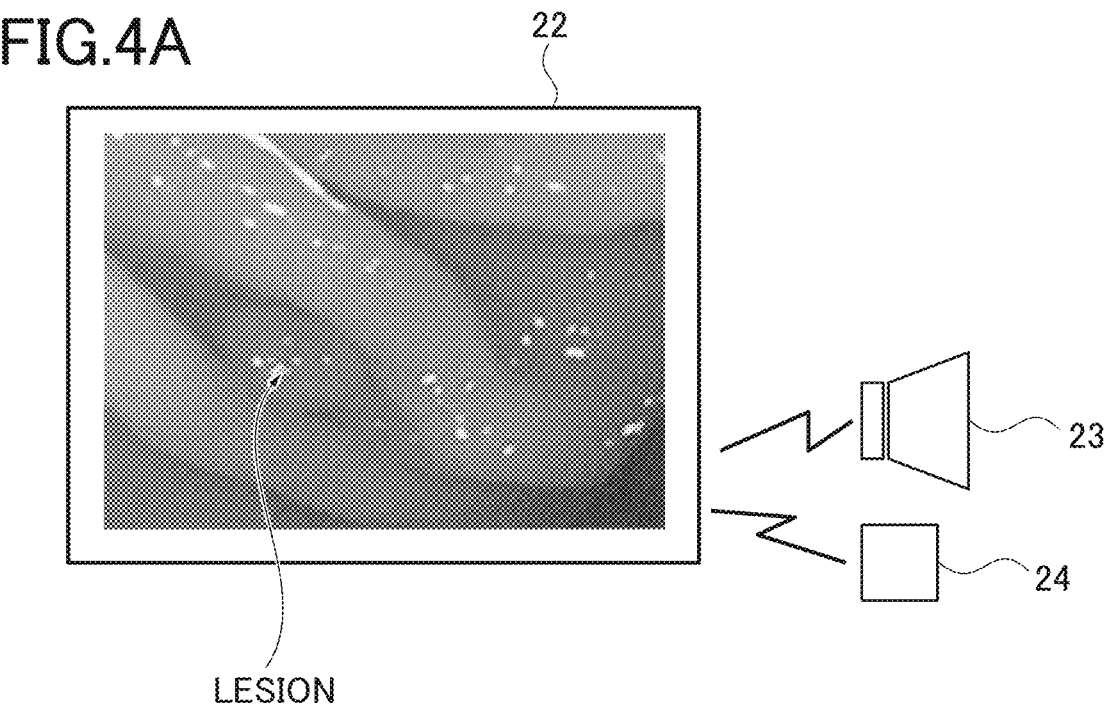
FIGS. 4A-4B are views showing examples of endoscopic images displayed on a display and states of a sound output part and a vibration part.

The image information acquisition part 31 converts the image signal input from the imaging part 41 of the endoscope device 40, applies appropriate image processing, and displays the processed image on the display 22 in real time (see FIG. 4A). In this embodiment, the video image and/or the still image captured by the imaging part 41 are displayed on the display 22. However, images displayed on the display 22 are not limited thereto. For example, a three-dimensional image generated based on the video image may be displayed thereon. The processed endoscopic image is then sent to the lesion information acquisition part 32.

The lesion information acquisition part 32 executes image recognition processing, such as feature extraction and pattern matching, based on the endoscopic image processed in the image information acquisition part 31. The lesion information acquisition part 32 then detects a lesion automatically and acquires various information related to a lesion (lesion information) therefrom.

To be specific, the lesion information acquisition part 32 automatically detects a tumor, a polyp, bleeding, diverticulum, stool, vascular dysplasia, peritoneal dissemination, pleural dissemination, and other lesions through the image recognition processing based on, for example, a laryngoscopic video image of nasal cavity, pharynx, larynx, and esophagus; a bronchoscopic image of trachea and bronchus;

an upper gastrointestinal endoscopic video image of esophagus, stomach, and duodenum; a small intestine endoscopic video image of the small intestine; a colonoscopic video image of the large intestine; a biliary endoscopic video image of bile duct; a pancreatic duct endoscopic video image of pancreatic duct; a thoracoscopic video image of inside of chest cavity; a laparoscopic video image of inside of abdominal cavity; a cystoscopic video image of urethra and bladder; an arthroscopic video image of inside of a joint; and a vascular endoscopic image of blood vessels, such as coronary arteries.

The lesion detection through the image recognition processing executed in the lesion information acquisition part 32 may be realized by means of any known technologies. Further, the lesion detection may preferably be realized by means of the method in which a plurality of frames are analyzed by artificial intelligence, as described in the non-Patent Literature 1, "Learning Spatiotemporal Features with 3D Convolutional Networks". With this method, it is possible to detect a lesion with higher accuracy. Here, the lesion detection realized by the lesion information acquisition part 32 is a result that an artificial intelligence (computer) mechanically estimates as a lesion based on the image recognition technology, learning function, and the like. With the development of the artificial intelligence, it is now possible to automatically detect a lesion with higher accuracy and to acquire more detailed information, such as a type and a status/condition of the lesion. The endoscope observation assistance apparatus 100 of this embodiment utilizes the detection results acquired by the artificial intelligence in order to assist the pathological diagnosis by a doctor.

The lesion information acquired by the lesion information acquisition part 32 is associated with the corresponding endoscopic image and is output to the lesion disappearance determination part 34. Examples of the lesion information are flag information indicating the lesion detection, a position and a size of the detected lesion in the endoscopic image, as well as the status or condition of the detected lesion. Additionally, it is preferable to include a lesion classification result through the image recognition processing, particularly, a lesion classification result, such as a tumor, a polyp, bleeding, diverticulum, stool, vascular dysplasia, peritoneal dissemination, and pleural dissemination.

The confirmation information acquisition part 33 acquires confirmation information input from the input part 21. To be specific, the confirmation information acquisition part 33 displays, for example, an imaging button for capturing a still image and a lesion confirmation button on the display 22. Alternatively, these buttons may be prepared on the keyboard in advance. The doctor makes an in-vivo observation by visually checking the endoscopic image displayed on the display 22 or by visually checking the inside of the body directly with a microscope, and manipulates the imaging button or the lesion confirmation button of the input part 21 when the doctor confirms the presence of a lesion. This operation signal is input to the confirmation information acquisition part 33 as confirmation information. Here, this embodiment is provided with the confirmation information acquisition part 33 to assist the endoscopic observation more efficiently. However, it is not necessary to provide the confirmation information acquisition part 33.

The lesion disappearance determination part 34 determines whether or not the lesion has disappeared from the endoscopic image based on the endoscopic image acquired by the image information acquisition part 31 and the lesion information acquired by the lesion information acquisition part 32. Additionally, the lesion disappearance determination part 34 of this embodiment determines whether or not the lesion has disappeared from the endoscopic image without the doctor's confirmation of the lesion based on the confirmation information acquired by the confirmation information acquisition part 33. The determination result is then output to the notification part 35.

The notification part 35 issues an alarm notification based on the determination result of the lesion disappearance determination part 34. The notification part 35 controls the sound output part 23 and the vibration part 24 to generate an alarm sound with the sound output part 23 and to vibrate the vibration part 24 when the lesion disappearance determination part 34 determines that the lesion has disappeared from the endoscopic image without the doctor's confirmation of the lesion. With the alarm sound and the vibration, it is possible to notify the doctor that the automatically detected lesion has disappeared from the endoscopic image without the doctor's confirmation of the lesion, so as to draw the doctor's attention.

Here, the alarm sound may be generated while changing the tone, the message, the volume, and/or the pitch of the sound depending on the classification result of the lesion. Additionally, the vibration may be generated while changing the wavelength and/or the magnitude of the vibration depending on the classification result of the lesion. Further, the alarm sound and/or the vibration may be changed in accordance with a weight determined based on the classification results of and the status level of the lesion. With this, it is possible to draw the doctor's attention more strongly so as to suggest the doctor for more careful observation.

The lesion information output part 36 displays the endoscopic image corresponding to the lesion detected by the lesion information acquisition part 32 on the display 22 as the output destination and stores the endoscopic image in the memory 17. With this, it is always possible for the doctor to check the endoscopic image and the lesion information for pathological diagnosis after the inspection. As a result, the assistance performance of the endoscopic observation improves while reducing the memory capacity.

The lesion information is preferably displayed on the display 22 and stored in the memory 17 in association with the endoscopic image. For example, the lesion in the endoscopic image on the display 22 may be enclosed by a line. With this, it is possible to facilitate the doctor to confirm the position of the automatically detected lesion and to draw the doctor's attention.

Further, an alarm may be displayed in the image on the display 22. In such a case, it is preferable not to display the lesion information in the endoscopic image in order to suppress the influence on the visibility of the endoscopic image. For example, the color of the area other than the endoscopic image may be changed to draw the doctor's attention. To be specific, the areas (corners), which are outside a displaying area 22a for the endoscopic image, on the screen of the display 22 may be used as an alarm displaying area 22b, as illustrated in, for example, FIG. 5A. As illustrated in FIG. 5A, the alarm displaying area 22b is displayed in an initial color (e.g., black) before the lesion, such as a polyp, is detected. Also, the color right after the detection of a lesion remains black.

When the lesion disappears from the endoscopic image after the detection of the lesion, the alarm displaying area 22b is displayed in a conspicuous color (e.g., red), as illustrated in FIG. 5B. Alternatively, the alarm displaying area 22b may be blinked. FIG. 5C is a variant of the display when the lesion disappears. In this case, the outer edge of the screen is defined as the alarm displaying area 22b and is displayed in red when the lesion disappears. As described herein, the color or the like of the alarm displaying area 22b, which is provided in addition to the displaying area 22a for the endoscopic image, is changed to encourage the doctor to check the endoscopic image. Therefore, it is possible for the doctor to recognize the disappearance of the lesion not only by sound and vibration but also by vision.

FIGS. 5D, 5E, 5F are other examples of the display 22 for issuing an alarm notification by changing the color. In these examples, the displaying areas 22a for the endoscopic image have substantially oval shapes, such that the inner peripheral edges of the alarm displaying areas 22b have arc shapes. Apart from this, the alarm displaying areas 22b are displayed in accordance with the similar processing as those in FIGS. 5A, 5B, 5C, thereby achieving the similar effects.

Further, since the endoscopic image and the lesion information are stored in the memory 17, it is possible to provide more detailed information about the lesion when the doctor conducts pathological diagnosis after the inspection.

An example of the endoscope observation assistance process executed by the endoscope observation assistance apparatus 100 as configured above will be described with reference to FIG. 3 flowchart. First, the doctor operates the operation part 43 of the endoscope device 40 to insert the insertion part 42 into the body of a patient to be observed. Subsequently to the insertion of the insertion part 42, the endoscopic image inside the body is captured by the imaging part 41 in real time.

In Step S1, the image information acquisition part 31 acquires the endoscopic image (frame) captured by the imaging part 41, performs image processing, and displays the image-processed image on the display 22. The processing from Step S2 is performed based on the acquired endoscopic image. Here, this processing may be executed every frame or every several frames.

In Step S2, the lesion information acquisition part 32 executes the automatic detection of a lesion by means of the above-described image recognition processing and learning functions based on the endoscopic image acquired by the image information acquisition part 31. FIG. 4A shows an example of the endoscopic image with a lesion. In this case, no notification is given by the sound output part 23 or the vibration part 24 although the lesion has been automatically detected. When detecting a lesion, the lesion information acquisition part 32 acquires the position and the size of the lesion in the endoscopic image as well as the status or condition of the lesion, thereby generating the lesion information. When a plurality of lesions are detected in a single endoscopic image, the image information acquisition part 32 generates the lesion information for each lesion.

In Step S3, it is determined whether or not the lesion information acquisition part 32 has detected a lesion. When no lesion is detected (NO), the program skips the processing of Steps S4 to S9 and proceeds to Step S10.

When a lesion is detected in Step S3, the program proceeds to Step S4, in which the confirmation information acquisition part 33 acquires confirmation information in order to determine whether or not the lesion confirmation operation has been conducted by the doctor. The program then proceeds to Step S5. In Step S5, the endoscopic image of the next frame is acquired and displayed on the display 22 by the image information acquisition part 31 and the lesion is detected by the lesion information acquisition part 32, so as to track the lesion in the confirmation information endoscopic image. In the next Step S6, it is determined whether or not the lesion being tracked has disappeared from the endoscopic image.

When it is determined in Step S6 that the lesion has not been disappeared (NO), the program returns to Step S4 to acquire the confirmation information and proceeds to Step S5 to continue tracking the lesion. As described above, no notification that the lesion has been automatically detected is generated while the lesion is appearing on the endoscopic image. Therefore, it is possible for the doctor to conduct the pathological diagnosis and the like while observing the endoscopic image displayed on the display 22 without being affected by the automatic detection result and the like unnecessarily.

When it is determined in Step S6 that the lesion has disappeared (YES), the program proceeds to Step S7, in which it is determined whether or not the confirmation information has been acquired with respect to the endoscopic image captured before the lesion disappearance. When it is determined that the confirmation information has been acquired (YES), the program proceeds to Step S9. In Step S9, the lesion information output part 36 displays the endoscopic image captured before the lesion disappearance and the lesion information on the display 22 and stores the endoscopic image and the lesion information in the memory 17.

As described above, when the confirmation information is acquired, it is possible to determine that the lesion automatically detected by the lesion information acquisition part 32 has been confirmed by the doctor, too. That is, the signal of the confirmation information is input to the assistance apparatus body 10 when the doctor who observes the endoscopic image and/or the microscope image sends an instruction through the input part 21 to capture a still image including the lesion or sends a confirmation instruction through the input part 21 in response to the detection of the lesion. If an instruction to capture a still image is sent, the lesion information output part 36 displays and stores the still image. If only a confirmation instruction is sent, the lesion information output part 36 displays and stores the endoscopic image (frame) captured before the lesion disappearance.

On the other hand, when it is determined in Step S7 that the confirmation information from the doctor has not been acquired before the lesion disappearance even though the lesion has disappeared (NO), the program proceeds to Step S8 to generate an alarm notification. This represents a case in which the automatic detection result of the lesion by the lesion information acquisition part 32 does not match the determination result of the lesion by the doctor or a case in which the confirmation operation has not been conducted by the doctor even though the doctor has confirmed that the automatic detection result matches the determination result. In these cases, the program proceeds to capture an image of another area.

Figure 4B:
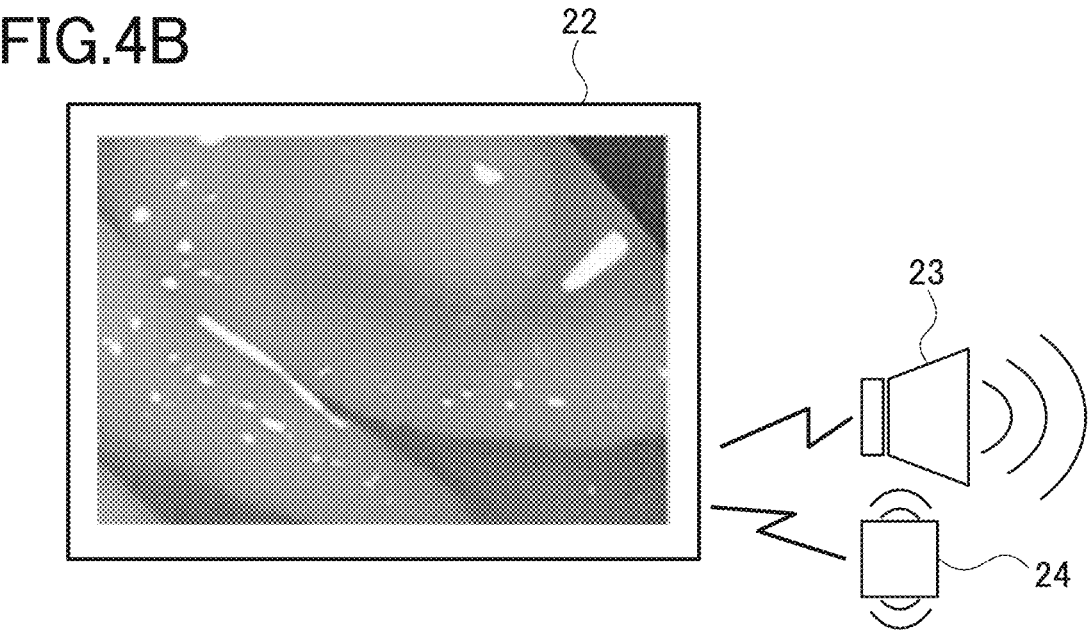

With the alarm notification processing in Step S8, the notification part 35 controls the sound output part 23 to generate an alarm sound and controls the vibration part 24 to vibrate. FIG. 4B shows an example of the endoscopic image in which the lesion has disappeared as well as a schematic image in which the alarm sound is generated by the sound output part 23 and the vibration part 24 vibrates. Additionally, as shown in FIGS. 5B, 5C, 5E, 5F, the alarm may be notified by displaying or blinking a prominent color, such as red, in the alarm displaying area 22b on the screen of the display 22.

With the alarm sound and vibration as well as the alarm notification on the display 22, it should be possible to let the doctor notice that the doctor has not confirmed the lesion automatically detected by the computer. That is, it is possible that the doctor does not consider the automatically detected lesion as a lesion or the doctor overlooks the lesion. It should be noted that the alarm notification is preferably made within one (1) second after the lesion disappearance. With this, it is possible to suppress the continuation of the endoscopic inspection without the lesion confirmation by the doctor. Additionally, it is possible to operate the operation part 43 backward to return the imaging area of the imaging part 41 to an area before the lesion disappearance. As a result, it is possible to reconfirm the presence of or status of the lesion, thereby improving the accuracy of the pathological diagnosis by the doctor.

The program then proceeds to Step S9, in which the lesion information output part 36 displays the endoscopic image captured before disappearance of the automatically detected lesion and the lesion information on the display 22 (or another display), as well as stores the endoscopic image and the lesion information in the memory 17. It is possible for the doctor to observe the area suspected of a lesion even with the endoscopic image displayed on the display 22. Additionally, it is possible for the doctor to reconfirm the endoscopic image of the lesion and the lesion information stored in the memory 17 after the inspection. The program then proceeds to Step S10.

In Step S10, it is determined whether or not the capturing of the endoscopic image by the endoscope device 40 is completed. When it is determined that the capturing of the image is completed (YES), the endoscope observation assistance process is ended as the inspection is completed. On the other hand, when it is determined that the capturing is ongoing (NO), the program returns to Step S1 to continue the endoscope observation assistance process for the next endoscopic image.

As described in the above, the endoscope observation assistance apparatus 100 of this embodiment includes the image information acquisition part 31, the lesion information acquisition part 32, the lesion disappearance determination part 34, and the notification part 35. The image information acquisition part 31 is configured to acquire the image of the luminal organs captured by the endoscope device 40 and to display the captured image on the display 22. The lesion information acquisition part 32 is configured to detect a predetermined lesion based on the captured image and to acquire the lesion information regarding the lesion. The lesion disappearance determination part 34 is configured to track the lesion based on the captured image and the lesion information and to determine whether or not the lesion has disappeared from the captured image. The notification part 35 is configured to notify the determination result when the lesion disappearance determination part 34 determines that the lesion has disappeared from the captured image.

Additionally, the endoscope observation assistance method of this embodiment includes a step of acquiring the captured image of the luminal organs captured by the endoscope device 40, a step of detecting a predetermined lesion based on the captured image and acquiring the lesion information regarding the lesion, a step of tracking the lesion based on the captured image and the lesion information and determining whether or not the lesion has disappeared from the captured image, and a step of notifying the determination result when it is determined that the lesion has disappeared from the captured image.

Additionally, the program for executing the endoscope observation assistance method of this embodiment causes a computer to function as a means of acquiring the captured image of the luminal organs captured by the endoscope device 40, a means of detecting a predetermined lesion based on the captured image and acquiring the lesion information regarding the lesion, a means of tracking the lesion based on the captured image and the lesion information and determining whether or not the lesion has disappeared from the captured image, and a means of notifying the determination result when it is determined that the lesion has disappeared from the captured image.

Accordingly, in this embodiment, it is possible for the operator, such as the doctor, to conduct the pathological diagnosis, treatment, and the like while observing the luminal organs by visually checking the captured image (endoscopic image) displayed on the display 22. Further, it is possible to automatically detect a lesion with high accuracy based on the captured image. In addition, while the lesion appears on the captured image, the automatic detection result is not notified prior to the doctor's decision. Therefore, it is possible for the doctor to conduct the pathological diagnosis without being affected by the automatic detection result unnecessarily.

On the other hand, when the lesion disappears from the captured image, a notification is issued. Therefore, it is possible for the doctor to notice that the detected lesion has disappeared from the captured image. If the doctor himself/herself has confirmed the lesion on the captured image, it is possible for the doctor to notice that his/her diagnostics result matches the automatic detection result. As a result, the automatic detection result may be used as a good ground to support the reliability of the doctor's diagnosis. Additionally, it is possible to suggest the doctor for reobservation around the lesion and for careful observation. Accordingly, it is possible to improve the performance of the observation assistance using the endoscope and to provide the endoscope observation assistance apparatus 100, the endoscope observation assistance process, and the program thereof that enables the doctors to observe the lesion more easily and accurately.

As described above, in this embodiment, it is possible to automatically detect the lesion with high accuracy, and a notification is issued when the automatically detected lesion disappears from the captured image. Therefore, it may be suitably used for training of pathological diagnosis using the endoscope. That is, even if an inexperienced doctor continues pathological diagnosis based on a captured image without noticing the lesion, the doctor is promptly notified that the lesion has disappeared from the captured image. With this, it is possible for the doctor to notice the overlooking and to conduct reobservation or the like. Additionally, the notification is not issued while the lesion appears on the captured image. With this, it is possible for the doctor to conduct the pathological diagnosis without being affected by the automatic detection result unnecessarily. As a result, it is possible to improve the pathological diagnosis ability of the doctor.

In this embodiment, the notification part 35 is configured to notify the determination result by outputting a predetermined notification sound from the sound output part 23. Additionally, the notification part 35 is configured to notify the determination result by vibrating the vibrator (vibration part 24). With the notification sound and the vibration, it is possible to draw the doctor's attention more strongly so as to clearly notify the doctor that the lesion has disappeared from the captured image.

This embodiment includes the lesion information output part 36 configured to output the captured image captured before the lesion disappearance to the predetermined output destination (e.g., display 22, memory 17) when the lesion disappearance determination part 34 determines that the lesion has disappeared from the captured image. With this, it is always possible for the doctor to check the endoscopic image and the lesion information for pathological diagnosis after the inspection, as well as to improve the assistance performance of the endoscopic observation.

This embodiment includes the input part 21 configured to receive the confirmation instruction of the lesion from the operator. The notification part 35 is configured to notify the determination result when the lesion disappearance determination part 34 determines that the lesion has disappeared from the captured image and no confirmation instruction has been input through the input part 21. That is, even if the lesion disappears, a notification is not issued as long as the doctor, who is the operator, has confirmed the lesion. With this, it is possible to minimize the notification and to assist the endoscopic observation efficiently.

Second Embodiment

Next, an endoscope observation assistance apparatus of a second embodiment will be described. In the first embodiment, an alarm notification for notifying that a lesion has disappeared is issued when it is determined that the lesion has disappeared from an endoscopic image. In the second embodiment, an alarm notification is issued to notify lesion detection when a short time period passes after the lesion is detected on an endoscopic image. That is, regardless of whether or not the lesion disappears from the endoscopic image, the alarm notification is issued shortly after the detection.

Since the endoscope observation assistance apparatus of the second embodiment includes the same basic configuration as that of the first embodiment except that the lesion disappearance determination part 34 is not provided, the detailed description will be omitted. The confirmation information acquisition part 33 may also be omitted. The endoscope observation assistance method of the second embodiment includes a step of acquiring a captured image of luminal organs captured by an endoscope device 40, a step of detecting a predetermined lesion based on the captured image and acquiring lesion information regarding the lesion, and a step of notifying that the lesion has been detected when a short time period passes after the lesion detection. The program for executing the endoscope observation assistance method of the second embodiment causes a computer to function as a means of acquiring a captured image of luminal organs captured by the endoscope device 40, a means of detecting a predetermined lesion based on the captured image and acquiring lesion information regarding the lesion, and a means of notifying that the lesion has been detected when a short time period passes after the lesion detection.

In the endoscope observation assistance apparatus of the second embodiment, the lesion information acquisition part 32 sends a signal to the notification part 35 when detecting a lesion, such as a polyp. The notification part 35 does not notify in real time when the lesion is detected but notifies that the lesion has been automatically detected when a short time period passes after the lesion detection, i.e., when a predetermined time period passes. Similar to the first embodiment, this notification is issued by, for example, generating an alarm sound from the sound output part 23, vibrating the vibration part 24, and/or changing the color in the alarm displaying area 22*b* shown in FIG. 5.

It should be noted that the "short time period" is a time period required for the doctor, who recognizes a lesion which is appeared in an endoscopic image, to determine that there is a lesion. To be specific, the "short time period" is preferably 30 ms to 2,000 ms. It is further preferable to be able to arbitrarily set or change the "short time period". With this, it is possible to set a suitable time period according to the doctors or the like even if the determination time varies due to proficiency levels of endoscopic inspection, ages, etc. of the doctors. As a result, it is possible to realize a more efficient inspection and to improve the usability of the endoscope device 40.

As described above, it is possible to secure a time period required for the doctors to determine the lesion based on the endoscopic image by notifying the automatic lesion detection after the short time period passes. Accordingly, it enables the doctor to determine the lesion by himself/herself without being affected by the automatic lesion detection result of the lesion information acquisition part 32.

Since the notification to notify that the lesion information acquisition part 32 has detected a lesion is made after the short time period, it is possible for the doctors to confirm whether or not the self-determination matches the automatic detection result by the artificial intelligence. Accordingly, it is possible to further increase the accuracy of the determination by the doctors.

The second embodiment may be suitably used for training of pathological diagnosis. For example, if an inexperienced doctor conducts endoscopic observation early in training, the short time period may be set relatively long so as to give the doctor more time to make decision. By setting the "short time period" to be gradually shortened each time the training is repeated, it makes the doctor possible to make decision faster.

As describe above, the artificial intelligence analyzes the plurality of image frames of the captured images. Therefore, it is possible to diagnose the lesion with higher accuracy, compare with the case where the analysis is made with a single image frame. In the conventional technology in which a notification of lesion detection is issued in real time, there is a limit to increasing the number of image frames to be analyzed as the priority is given to the processing speed. On the other hand, in this embodiment, a notification is issued when a predetermined time period passes after lesion detection, and, in the first embodiment, a notification is made when the lesion has disappeared. Therefore, it is possible to secure a predetermined analysis time, thereby analyzing more image frames. As a result, it is possible to acquire more detailed information, such as the type and the degree of the lesion, thereby improving the accuracy of the lesion detection and the accuracy of the lesion information by the artificial intelligence.

As described above, the embodiments of this disclosure have been described in detail with reference to the drawings. However, the above embodiments are merely examples of the disclosure. The disclosure is not limited to the above-described embodiments. Any modifications made without departing from the gist of this disclosure are of course included in the scope of this disclosure.

For example, in the above embodiments, the endoscope device 40, which includes the imaging part 41, the insertion part 42, and the operation part 43, is connected to the assistance apparatus body 10. The assistance apparatus body 10 processes the captured image captured by the imaging part 41 and displays the processed image on the display 22. However, an endoscope unit which includes, in addition to the imaging part 41, the insertion part 42, and the operation part 43, an imaging function for the captured image, such as a video tuner and a display, may be used. Further, such a display of the endoscope unit may also be used as the display 22 of the endoscope observation assistance apparatus 100, or a separate display 22 may be provided.

Further, the endoscope unit may be configured to include an information processing apparatus, which includes an image processing section configured to automatically detect a lesion based on the captured image. In this case, the automatic detection result of the lesion by the image processing section may be acquired by the lesion information acquisition part 32 of the assistance apparatus body 10 and be used for the endoscope observation assistance process. With this, it is possible to effectively use the automatic detection result of the endoscope unit so as to reduce processing load in the assistance apparatus body 10, thereby accelerating the operating speed.

Further, the endoscope unit including the information processing apparatus may include the endoscope observation assistance apparatus 100 of each embodiment. That is, the endoscope unit may be provided with the sound output part 23 and the vibration part 24, and the information processing apparatus of the endoscope unit may also be used as the information processor 20 in which the endoscope observation assistance program of each embodiment is installed. With this, it is possible to provide the endoscope unit including the endoscope observation assistance apparatus. Therefore, it is possible to make a sale as the endoscope unit including the endoscope observation assistance apparatus. Alternatively, it is possible to solely sell the endoscope observation assistance program to be installed in and used by an existing endoscope unit. Additionally, it is possible to make each device compact and/or simple to simplify its handling.

In the above embodiments, the notification to notify the doctor of the lesion disappearance from the endoscopic image is issued by the notification sound and/or the vibration. However, a lighting part, such as an LED, may be provided to notify an error by flashing the light. In this case, the lighting color and/or the blinking interval may be adjusted depending on the weight of the lesion and/or the type of the lesion so as to realize more understandable notification.

Further, a time measuring part to measure a time for inserting the insertion part 42 may be provided to calculate the distance from the anal verge based on the insertion speed (may be measured by a speed meter or an average insertion speed may be used) and the insertion time of the insertion part 42 if a colonoscope is used as the endoscope. Then, the calculation result may be displayed on the display 22. The distance from the anal verge to the lesion may be displayed when the lesion image is displayed on the display 22 after the lesion disappearance from the captured image. With this, it is possible for the doctor to determine how many centimeters the endoscope device should be returned to capture the lesion easily and accurately, thereby improving the performance of the observation assistance for the lesion.

In the first embodiment, the alarm notification is issued when the lesion disappears, and in the second embodiment, the alarm notification is issued when the short time period passes after the lesion is detected. However, it should not be limited thereto. Depending on the purpose of the use, the alarm notification may be issued both when the lesion disappears as well as when the short time period passes after the lesion is detected. With this, it is possible to draw the doctor's attention more strongly.

The invention claimed is:

1. An endoscope observation assistance apparatus for assisting observation of a luminal organ with an endoscope, the apparatus comprising:
   a processor; and
   a non-transitory computer-readable medium having stored thereon executable instructions that, when executed by the processor, cause the endoscope observation assistance apparatus to:
      acquire a captured image of the luminal organ captured by the endoscope and display the captured image on a display;
      detect a predetermined lesion based on the captured image and acquire lesion information regarding the lesion;
      track the lesion based on the captured image and the lesion information and determine whether or not the lesion has disappeared from the captured image;
      determine that the endoscope observation assistance apparatus failed to receive an input of a confirmation instruction of the lesion by a doctor operating the endoscope before the lesion disappeared from the captured image; and
      issue a notification of a determination result upon determination that the lesion has disappeared from the captured image and that no confirmation instruction had been received;
   wherein the notification of the determination result is performed by a vibration of a vibrator which is changed in accordance with a weight determined based on classification results and status level of the lesion.

2. The apparatus according to claim 1, wherein the processor is further configured to control the endoscope observation assistance apparatus to output the captured image of the lesion captured before the lesion disappears to a predetermined output destination upon determination that the lesion has disappeared from the captured image.

3. The apparatus according to claim 1, wherein the processor is further configured to control the endoscope observation assistance apparatus to make the notification by outputting a predetermined alarm sound.

4. An endoscope observation assistance method, comprising:
   acquiring a captured image of a luminal organ captured by an endoscope;
   detecting a lesion based on the captured image and acquiring lesion information regarding the lesion;
   tracking the lesion based on the captured image and the lesion information and determining whether or not the lesion has disappeared from the captured image;
   determining that there is a failure to receive an input of a confirmation instruction of the lesion from a doctor operating the endoscope before the lesion disappeared from the captured image; and
   issuing a notification of a determination result upon determination that the lesion has disappeared from the captured image and that no confirmation instruction had been received;
   wherein issuing the notification of the determination result is performed by a vibration of a vibrator which is changed in accordance with a weight determined based on classification results and status level of the lesion.

* * * * *